United States Patent [19]

Rüger et al.

[11] Patent Number: 5,185,324
[45] Date of Patent: Feb. 9, 1993

[54] ENZYME-INHIBITING AMINO ACID DERIVATIVES, A PROCESS FOR THE PREPARATION THEREOF, AGENTS CONTAINING THESE, AND THE USE THEREOF

[75] Inventors: Wolfgang Rüger; Hansjörg Urbach; Dieter Ruppert; Bernward Scholkens, all of Taunus, Fed. Rep. of Germany

[73] Assignee: Hoechst Aktiengesellschaft, Frankfurt am Main, Fed. Rep. of Germany

[21] Appl. No.: 448,903

[22] Filed: Dec. 12, 1989

[30] Foreign Application Priority Data

Dec. 14, 1988 [DE] Fed. Rep. of Germany ....... 3842067

[51] Int. Cl.$^5$ .................... A61K 37/00; C07K 5/00
[52] U.S. Cl. ........................ 514/18; 530/331
[58] Field of Search .................. 514/19, 18; 530/331

[56] References Cited

FOREIGN PATENT DOCUMENTS 3626130 8/1986 Fed. Rep. of Germany ........ 514/19

OTHER PUBLICATIONS

CA 109:93623h: "Preparation of thiazole-and tetra-thiazole-containing . . . ", Raddatz et al., pp. 775-776 (1988).
ASM News, Jul. 1990, 56(7):368.

*Primary Examiner*—Lester L. Lee
*Assistant Examiner*—B. Celsa
*Attorney, Agent, or Firm*—Finnegan, Henderson, Farabow, Garrett & Dunner

[57] ABSTRACT

The present invention relates to compounds of the general formula I

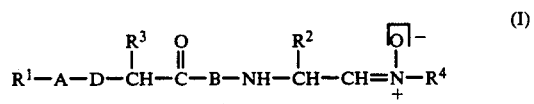

in which
A denotes a radical from the group comprising S, SO, SO$_2$, O, CO, CS or a direct bond,
B denotes the radical of an amino acid and
D denotes a CH$_2$ group or a radical —NR$^7$—, where R$^7$ can be hydrogen or a (C$_1$–C$_4$)alkyl radical;

and in which R$^1$ to R$^4$ are defined as indicated in the description, to a process for the preparation thereof, to agents containing these, and to the use thereof.

3 Claims, No Drawings

ENZYME-INHIBITING AMINO ACID DERIVATIVES, A PROCESS FOR THE PREPARATION THEREOF, AGENTS CONTAINING THESE, AND THE USE THEREOF

DESCRIPTION

The invention relates to enzyme-inhibiting amino acid derivatives which contain a nitrone structural element in the "$P_1$-$P_1'$ position", to a process for the preparation thereof, to agents containing these, and to the use thereof.

Many derivatives of amino acids, dipeptides and oligopeptides which are able to inhibit aspartyl proteases such as, for example, the enzyme renin are known. A review of them is provided, for example, by W. Greenlee, Pharmac. Res. 4 (1987) 364. The most effective of these compounds are based on the principle of transition-state analogs and contain in the appropriate position ($P_1$-$P_1'$ in the notation of Schechter and Berger, Biochem. Biophys. Res. Commun. 27 (1967) 157) a hydroxyl isoster, for example in the form of a statin or norstatin derivative, or a dihydroxyl isoster, for example in the form of an aminodiol derivative.

The invention has the object of seeking new compounds which differ from the known structures, i.e. do not have the hydroxyl functionality regarded as essential in the known transition-state analogs and nevertheless are highly effective inhibitors of aspartyl proteases such as, for example, renin and retroviral proteases such as, for example, HIV protease in vitro and in vivo.

This object is achieved according to the invention by the compounds of the general formula I

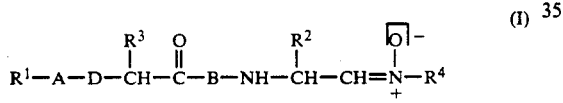

in which $R^1$ denotes hydrogen, ($C_1$-$C_{18}$)-alkyl, ($C_3$-$C_7$)-cycloalkyl each of which can be substituted by amino, hydroxyl, mercapto, halogen, ($C_1$-$C_4$)-alkoxy, mono- or di-($C_1$-$C_4$)-alkylamino, carboxyl, ($C_1$-$C_4$)-alkoxycarbonyl, phenoxy, phenyl-($C_1$-$C_4$)-alkoxy, phenyl-($C_1$-$C_4$)-alkoxycarbonyl or a radical —$CONR^5R^6$; ($C_1$-$C_4$)-alkoxy, ($C_6$-$C_{14}$)-aryl, ($C_6$-$C_{14}$)-aryl-($C_1$-$C_4$)-alkyl, ($C_6$-$C_{14}$)-aryl-($C_1$-$C_4$)-alkoxy, it being possible for each aryl radical to be substituted by one, two or three radicals from the group comprising ($C_1$-$C_6$)-alkyl, amino, mono- or di-($C_1$-$C_4$)-alkylamino, amino-($C_1$-$C_4$)-alkyl, hydroxy-($C_1$-$C_4$)-alkyl, mono- or di-($C_1$-$C_4$)-alkylamino-($C_1$-$C_4$)-alkyl, hydroxyl, ($C_1$-$C_4$)-alkoxy, halogen, formyl, ($C_1$-$C_4$)-alkoxycarbonyl, carboxamido, mono- or di-($C_1$-$C_4$)-alkylaminocarbonyl or nitro or by one methylenedioxy radical; Het or Het-($C_1$-$C_4$)-alkyl, where Het represents a 5-, 6- or 7-membered heterocyclic ring which can be benzo-fused and either aromatic, partially hydrogenated or completely hydrogenated and which can contain as heteroelements one or two radicals from the group comprising N, O, S, NO, SO or $SO_2$ and can be substituted by one or two radicals from the group comprising ($C_1$-$C_4$)-alkyl, ($C_1$-$C_4$)-alkoxy, ($C_1$-$C_4$)-alkoxycarbonyl, hydroxyl, halogen, amino, mono- or di-($C_1$-$C_4$)-alkylamino, or denotes a radical —$NR^5R^6$, where and $R^6$ denote, identically or differently and independently of one another, hydrogen, ($C_1$-$C_8$)-alkyl which can be substituted by amino, ($C_1$-$C_4$)-alkylamino, di-($C_1$-$C_4$)-alkylamino, hydroxyl or ($C_1$-$C_4$)-alkoxy, or ($C_3$-$C_7$)-cycloalkyl, mercapto, ($C_1$-$C_4$)-alkylthio, phenylthio, ($C_1$-$C_4$)-alkoxycarbonyl, carboxyl, ($C_6$-$C_{14}$)-aryl which can be substituted in the aryl radical as described for $R^1$, or Het or Het-($C_1$-$C_4$)-alkyl, where Het is defined as described for $R^1$, or where $R^5$ and $R^6$ form, together with the nitrogen atom carrying them, a 5- to 12-membered ring which can be mono- or bicyclic and can contain as further ring members also 1 or 2 nitrogen atoms, 1 sulfur atom or 1 oxygen atom and can be substituted by ($C_1$-$C_4$)-alkyl;

A denotes a radical from the group comprising S, SO, $SO_2$, O, CO, CS or a direct bond;

D denotes a $CH_2$ group or a radical —$NR^7$—, where $R^7$ can be hydrogen or a ($C_1$-$C_4$)-alkyl radical;

$R^3$ denotes ($C_6$-$C_{14}$)-aryl, ($C_6$-$C_{14}$)-aryl-($C_1$-$C_4$)-alkyl, it being possible for each aryl radical to be substituted by one, two or three radicals as described under $R^1$, or thienyl or thienyl-($C_1$-$C_4$)-alkyl, it being possible for each thiophene radical to be substituted by one or two radicals from the group comprising ($C_1$-$C_4$)-alkyl, ($C_1$-$C_4$)-alkoxy or halogen, or 2-, 3- or 4-pyridyl or 2-, 3- or 4-pyridyl-($C_1$-$C_4$)-alkyl, it being possible for the pyridine radical to be substituted by one or two radicals from the group comprising ($C_1$-$C_4$)-alkyl, ($C_1$-$C_4$)-alkoxy or halogen;

B denotes a radical, which is linked N-terminal via —$NR^8$— with $R^1$—A—D—$CHR^3$—CO— and C-terminal and via —CO— with

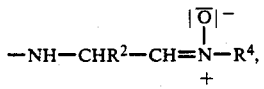

of an amino acid from the series comprising phenylalanine, histidine, tyrosine, tryptophan, methionine, leucine, isoleucine, asparagine, aspartic acid, β-2-thienylalanine, β-3thienylalanine, β-2-furylalanine, β-3-furylalanine, lysine, ornithine, valine, alanine, 2,4-diaminobutyric acid, arginine, 4-chlorophenylalanine, methionine sulfone, methionine sulfoxide, 2-pyridylalanine, 3-pyridylalanine, cyclohexylalanine, cyclohexylglycine, im-methylhistidine, O-methyltyrosine, O-benzyltyrosine, O-tert.-butyltyrosine, phenylglycine, 1-naphthylalanine, 2-naphthylalanine, 4-nitrophenylalanine, norvaline, β-2-benzo[b]-thienylalanine, β-3-benzo-[b]thienylalanine, 2-fluorophenylalanine, 3-fluorophenylalanine, 4-fluorophenylalanine, norleucine, cysteine, S-methylboxylic acid, homophenylalanine, DOPA, O-dimethyl-DOPA, 2-amino-4-(2-thienyl)-butyric acid, benzodioxol-5-yl-alanine, N-methyl-histidine, 2-amino-4-(3-thienyl)-butyric acid, 3-(2-thienyl)-serine, (Z)-dehydrophenylalanine, (E)-dehydrophenylalanine, (1,3-dioxolan-2-yl)alanine, N-pyrrolylalanine, (1-, 3- or 4-pyrazolyl)alanine, (4-thiazolyl)alanine, (2-, 4- or 5-pyrimidyl)alanine, cyclopentylglycine, tert.butylglycine or phenylserine, and $R^8$ denotes hydrogen, ($C_1$-$C_6$)-alkyl, formyl, ($C_1$-$C_6$)-alkoxycarbonyl or benzyloxycarbonyl;

$R^2$ denotes hydrogen, ($C_1$-$C_{10}$)-alkyl, ($C_4$-$C_7$)-cycloalkyl, ($C_4$-$C_7$)-cycloalkyl-($C_1$-$C_4$)-alkyl, ($C_6$-$C_{14}$)-aryl, ($C_6$-$C_{14}$)-aryl-($C_1$-$C_4$)-alkyl or (heterocyclyl)-($C_1$-$C_4$)-alkyl, where the heterocycle has 4-7 ring members, of which 1 or 2 are sulfur and/or oxygen atoms; and $R^4$ denotes $(C_1-C_8)$-alkyl, $(C_3-C_8)$-cycloalkyl, $(C_3-C_8)$-cycloalkyl-$(C_1-C_4)$-alkyl, each of which can be substituted once, twice or three times by amino, hydroxyl, mercapto, halogen, $(C_1-C_4)$-alkoxy, mono- or di-$(C_1-C_4)$-alkylamino, carboxyl, guanidino, $(C_1-C_4)$-alkoxycarbonyl or a radical —$CONR^5R^6$, in which $R^5$ and $R^6$ are as defined above; $(C_8-C_{14})$-aryl, $(C_8-C_{14})$-aryl-$(C_1-C_4)$-alkyl, it being possible for the aryl radical to be substituted as described under $R^1$ and for the alkyl chain to be substituted as described above for $R^4$; Het or Het-$(C_1-C_4)$-alkyl, where Het is defined as described under $R^1$, and the alkyl chain can be substituted as described above for $R^4$;

as well as the physiologically tolerated salts thereof.

The centers of chirality in the compounds of the formula I can have the R or S or R,S configuration.

Alkyl can be straight-chain or branched. A corresponding statement applies to radicals derived therefrom, such as, for example, alkoxy, alkylthio, alkylamino, dialkylamino and alkanoyl.

Cycloalkyl also means alkyl-substituted radicals such as, for example, 4-methylcyclohexyl or 2,3-dimethylcyclopentyl.

Halogen represents fluorine, chlorine, bromine or iodine, and preferably represents fluorine or chlorine.

$(C_6-C_{14})$-Aryl is, for example, phenyl, naphthyl, biphenylyl or fluorenyl; phenyl is preferred. A corresponding statement applies to $(C_6-C_{14})$-aryl-$(C_1-C_4)$-alkyl. Examples of preferred radicals of this type are benzyl, α- and β-naphthylmethyl, halobenzyl and alkoxybenzyl.

A Het radical within the meaning of the above definition is, for example, pyrrolyl, furyl, thienyl, imidazolyl, pyrazolyl, oxazolyl, thiazolyl, pyridyl, pyrazinyl, pyrimidinyl, indolyl, quinolyl, isoquinolyl, quinoxalinyl, β-carbolinyl or a benzo-fused, cyclopenta-, cyclohexa- or cyclohepta-fused derivative of these radicals.

Preferred Het radicals are 2- or 3-pyrrolyl, phenylpyrrolyl, for example 4- or 5-phenyl-2-pyrrolyl, 2-furyl, 2-thienyl, 4-imidazolyl, methyl-imidazolyl, for example 1-methyl-2-, 4- or 5-imidazolyl, 1,3-thiazol-2-yl, 2-, 3- or 4-pyridyl, 1-oxido-2-,3- or 4-pyridinio, 1- or 2-pyrazinyl, 2-, 4- or 5-pyrimidinyl, 4-morpholinyl, 2-, 3- or 5-indolyl, substituted 2-indolyl, for example 1-methyl-, 5-methyl-, 5-methoxy-, 5-benzyloxy-, 5-chloro or 4,5-dimethyl-2-indolyl, 1-benzyl-2- or 3-indolyl, 4,5,6,7-tetrahydro-2-indolyl, cyclohepta[b]-5-pyrrolyl, 2-, 3- or 4-quinolyl, 4-hydroxy-2-quinolyl, 1-, 3- or 4-isoquinolyl, 1-oxo-1,2-dihydro-3-isoquinolyl, 2-quinoxalinyl, 2-benzofuranyl, 2-benzoxazolyl, 2-benzothiazolyl, benzo[e]indol-2-yl, β-carbolin-3-yl, 2-oxazolinyl, 4-alkyl-2-oxazolinyl or 4,5-dialkyloxazolinyl.

Salts of compounds of the formula I mean, in particular, pharmaceutically utilizable or non-toxic salts.

Salts of these types are formed, for example, from compounds of the formula I which contain acidic groups, for example carboxyl, with alkali metals or alkaline earth metals such as Na, K, Mg and Ca, as well as with physiologically tolerated organic amines such as, for example, triethylamine and tri-(2-hydroxyethyl)-amine.

Compounds of the formula I which contain basic groups, for example an amino group, form salts with inorganic acids such as, for example, hydrochloric acid, sulfuric acid or phosphoric acid and with organic carboxylic or sulfonic acids such as, for example, acetic acid, citric acid, benzoic acid, maleic acid, fumaric acid, tartaric acid and p-toluenesulfonic acid.

Preferred compounds of the formula I are those in which $R^1$ denotes methyl, ethyl, isopropyl, tert.-butyl, isobutyl, 2-hydroxyethyl, 2-methoxyethyl, carboxymethyl, 2-carboxyethyl, methoxycarbonylmethyl, 2-methoxycarbonylethyl, ethoxycarbonylmethyl, 2-ethoxycarbonylethyl, carbamoylmethyl, 2-carbamoylethyl, 2-aminoethyl, 2-dimethylaminoethyl, 2-morpholinoethyl, aminoisobutyl, 2-piperidinoethyl, aminopropyl, dimethylaminopropyl, methylaminopropyl, piperidinopropyl, morpholinopropyl, methylaminoisobutyl, dimethylaminoisobutyl, piperidinoisobutyl, morpholinoisobutyl, cyclopropyl, cyclobutyl, cyclopentyl or cyclohexyl, phenyl, 1- or 2-naphthyl, o-, m- or p-methylphenyl, o-, m- or p-hydroxyphenyl or o-, m- or p-aminophenyl, benzyl, 2-phenylethyl or α- or β-naphthylmethyl, unsubstituted or substituted heteroaryl, for example 2- or 3-pyrrolyl, 2-furyl, 2-thienyl, 2- or 4-imidazolyl, 1-methyl-2-, -4- or -5-imidazolyl, 1,3-thiazol-2-yl, 2-, 3- or 4-pyridyl, 1-oxido-2-, 3- or 4-pyridinio, 2-pyrazinyl, 2-, 4- or 5-pyrimidinyl, 2-, 3- or 4-quinolyl, 1-, 3- or 4-isoquinolyl or 2-benzoxazolyl, methoxy, ethoxy or n-butoxy or a radical —$NR^5R^6$, in which $R^5$ and $R^6$ denote, identically or differently and independently of one another, hydrogen, methyl, ethyl, propyl, butyl, isobutyl, sec.-butyl, tert.-butyl, aminoethyl, aminopropyl, methylaminoethyl, dimethylaminoethyl, methylaminopropyl, dimethylaminopropyl, hydroxyethyl, methoxyethyl, cyclohexylmethyl, mercaptoethyl, methylthioethyl, benzyl, 1-phenethyl, 2-phenethyl, 2-(3,4-dimethoxy)-phenethyl, 2-pyridylmethyl, 3-pyridylmethyl, or in which $R^5$ and $R^6$ form, together with the nitrogen atom carrying them, a pyrrolidine, piperidine, azepine, azocine, morpholine, piperazine, 4-methylpiperazine, 4-ethyl-piperazine, homopiperazine or thiomorpholine ring;

A denotes a radical from the group comprising S, SO, $SO_2$, O, CO or CS;

D denotes a $CH_2$ group, an NH group or an $N(CH_3)$ group;

$R^3$ denotes phenyl, 2-thienyl, 2-pyridyl, 1-naphthyl, phenyl-$(C_1-C_4)$-alkyl, 2-thienyl-$(C_1-C_4)$-alkyl, 2-pyridyl-$(C_1-C_4)$-alkyl, 1-naphthyl-$(C_1-C_4)$-alkyl, each of which is optionally substituted by one, two or three radicals from the group comprising, methyl, ethyl, isopropyl, tert.-butyl, methoxy, hydroxyl, fluorine, chlorine or nitro or one methylenedioxy radical;

B denotes a radical, which is linked N-terminal via —NH— with $R^1$—A—D—$CHR^3$—CO— and C-terminal via —CO— with

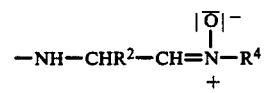

of an amino acid from the series comprising phenylalanine, histidine, tyrosine, tryptophan, methionine, leucine, isoleucine, asparagine, aspartic acid, β-2-thienylalanine, β-3-thienylalanine, β-2-furylalanine, β-3-furylalanine, lysine, ornithine, 2,4-diaminobutyric acid, arginine, norvaline, 4-chlorophenylalanine, methionine sulfone, methionine sulfoxide, 2-pyridylalanine, 3-pyridylalanine, cyclohexylalanine, cyclohexylglycine, im-methylhistidine, O-methyltyrosine, O-benzyltyrosine, O-tert.-butyltyrosine, phenylglycine, 1-naphthylalanine, 2-naphthylalanine, 4-nitrophenylalanine, norleucine, valine, alanine, cysteine, S-methylcysteine, N-methyl-histidine, benzodioxol-5-yl-alanine, 1,2,3,4-tetrahydroisoquinoline-3-carboxylic acid, homophenylalanine, 2-amino-4-(3-thienyl)butyric acid, (Z)-dehydrophenylalanine, (E)-dehydrophenylalanine, (1,3-dioxolan-2yl)alanine, (4-thiazolyl)alanine, (2, 4- or 5-pyrimidyl)alanine, (1-, 3- or 4-pyrazolyl)alanine, (2-, 3- or 4-fluorophenyl)alanine, cyclopentylglycine, tert.-butylglycine or phenylserine;

$R^2$ is as defined supra, and $R^4$ denotes methyl, ethyl, propyl, isopropyl, butyl, isobutyl, sec.-butyl, tert.-butyl, pentyl, isopentyl, neopentyl, sec.-pentyl, tert.-pentyl, hexyl, cyclopentyl, cyclohexyl, cycloheptyl, cyclopentylmethyl, cyclohexylmethyl, cycloheptylmethyl, phenyl, benzyl, phenylethyl, phenylpropyl, 2-, 3- or 4-pyridyl, 2-, 4- or 5-imidazolyl, (2-, 3- or 4-pyridyl)methyl, (2-, 4- or 5-imidazolyl)methyl, it being possible for the said alkyl and cycloalkyl radicals in each case to be substituted once or twice by amino, halogen mono- or di-($C_1$-$C_4$)-alkylamino, carboxyl, guanidino, ($C_1$-$C_4$)-alkoxycarbonyl or a radical —$CONR^5R^6$ in which $R^5$ and $R^6$ are as defined on pages 6 and 7; it being possible for the said phenyl radicals to be substituted once or twice by ($C_1$-$C_4$)-alkyl, methoxy, hydroxyl, amino, aminomethyl, fluorine, chlorine or trifluoromethyl, and it being possible for the said heteroaromatic radicals in each case to be substituted by one or two radicals from the series comprising ($C_1$-$C_4$)-alkyl, methoxy, fluorine, chlorine, bromine or trifluoromethyl, as well as the physiologically tolerated salts thereof.

Particularly preferred compounds of the formula I are those in which $R^1$ denotes methyl, ethyl, isopropyl, tert.-butyl, isobutyl, 2-hydroxyethyl, 2-methoxyethyl, carboxymethyl, 2-carboxyethyl, methoxycarbonylmethyl, 2-methoxycarbonylethyl, ethoxycarbonylmethyl, 2-ethoxycarbonylethyl, carbamoylmethyl, 2-carbamoylethyl, 2-aminoethyl, 2-dimethylaminoethyl, 2-morpholinoethyl, aminopropyl, aminoisobutyl, methylaminoisobutyl, dimethylaminoisobutyl, 2-piperidinoethyl, cyclopropyl, cyclobutyl, cyclopentyl or cyclohexyl, phenyl, 1- or 2-naphthyl, o-, m- or p-methylphenyl, o-, m- or p-hydroxyphenyl or o-, m- or p-aminophenyl, benzyl, 2-phenylethyl or α- or β-naphthylmethyl, unsubstituted or substituted heteroaryl, for example 2- or 3-pyrrolyl, 2-furyl, 2-thienyl, 2- or 4-imidazolyl, 1-methyl-2-, -4- or -5-imidazolyl, 1,3-thiazol-2-yl, 2-, 3- or 4-pyridyl, 1-oxido-2-, 3- or 4-pyridinio, 2-pyrazinyl, 2-, 4- or 5-pyrimidinyl, 2-, 3- or 4-quinolyl, 1-, 3- or 4- isoquinolyl or 2-benzoxazolyl, methoxy, ethoxy or n-butoxy or a radical —$NR^5R^6$, in which $R^5$ and $R^6$ denote, identically or differently and independently of one another, hydrogen, methyl, ethyl, propyl, butyl, isobutyl, sec.-butyl, tert.-butyl, hydroxyethyl, methoxyethyl, aminoethyl, aminopropyl, benzyl- or pyridylmethyl, or in which $R^5$ and $R^6$ form, together with the nitrogen atom carrying them, a pyrrolidine, piperidine, morpholine or piperazine ring;

A denotes a radical from the group comprising S, SO, $SO_2$, O, CO or CS;

D denotes a $CH_2$ group, an NH group or an $N(CH_3)$ group;

$R^3$ denotes aryl or arylmethyl, where aryl denotes phenyl, 2-thienyl, 2-pyridyl or 1-naphthyl, each of which is optionally substituted by hydroxyl, dihydroxyl, methoxy, dimethoxy, fluorine, chlorine or methylenedioxy;

B denotes a radical, which is linked N-terminal via —NH— with $R^1$—A—D—$CHR^3$—CO— and C-terminal via —CO— with

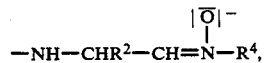

of an amino acid from the series comprising phenylalanine, histidine, leucine, β-2-thienylalanine, β-3-thienylalanine, lysine, norvaline, 2-fluorophenylalanine, 3-fluorophenylalanine, 4-fluorophenylalanine, norleucine, S-methylcysteine, (1,3-dioxolan-2-yl)alanine, (1-, 3- or 4-pyrazolyl)alanine, 4-thiazolylalanine, (2-, 4- or 5-pyrimidyl)alanine;

$R^2$ denotes isobutyl, cyclohexylmethyl, benzyl or (1,3-dithiolan-2-yl)methyl; and $R^4$ denotes methyl, ethyl, propyl, isopropyl, butyl, isobutyl, sec.-butyl, tert.-butyl, pentyl, isopentyl, neopentyl, sec.-pentyl, tert.-pentyl, hexyl, cyclopentyl, cyclohexyl, cyclopentylmethyl, cyclohexylmethyl, phenyl, benzyl, phenylethyl, 2-, 3- or 4-pyridyl, 2-imidazolyl, (2-, 3- or 4-pyridyl)methyl, 2-imidazolylmethyl, it being possible for the said alkyl and cycloalkyl radicals in each case to be substituted once or twice by amino, fluorine, chlorine, methylamino, ethylamino, dimethylamino, diethylamino, carboxyl, guanidino, methoxycarbonyl, ethoxycarbonyl, tert.-butyloxycarbonyl or a radical —$CONR^5R^6$, in which $R^5$ and $R^6$ are defined as on page 9, it being possible for the said phenyl radicals to be substituted once or twice by methyl, methoxy, hydroxyl, amino, aminomethyl, fluorine, chlorine or trifluoromethyl, and it being possible for the said heteroaromatic radicals to be substituted with, in each case, one or two radicals from the series comprising methyl, methoxy, fluorine, chlorine or trifluoromethyl, as well as the physiologically tolerated salts thereof.

The invention furthermore relates to a process for the preparation of compounds of the formula I, which comprises a) reacting a compound of the general formula II

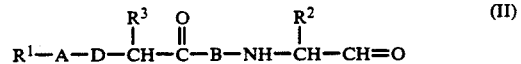

in which $R^1$, $R^2$, $R^3$, A, B and D have the same meaning as in formula I, with a hydroxylamine derivative of the general formula III

in which $R^4$ has the same meaning as in formula I, in an organic solvent such as, for example, diethyl ether, ethanol, benzene, toluene or in water or without any solvent at a temperature between −20° C. and the boiling point of the solvent, preferably between −20° C. and +60° C., with or without the presence of an acid, for example hydrogen chloride or acetic acid, which can be introduced, for example, in the form of the salts of the hydroxylamines of the formula III, with or without the presence of an auxiliary base such as, for example, sodium bicarbonate, sodium acetate, sodium carbonate, sodium ethanolate or potassium hydroxide, and with or without the presence of a water-extracting agent such as, for example, calcium chloride or molecular sieves, and, where appropriate, eliminating (a) protective group(s) temporarily introduced to protect other functional groups, or b) coupling a fragment with a terminal carboxyl group, or the reactive derivative thereof, with a corresponding fragment with a free amino group, where appropriate eliminating (a) protective group(s) temporarily introduced to protect other functional groups, and converting the compound obtained in this way into the physiologically tolerated salt thereof where appropriate.

The compounds of the general formula II can be prepared, for example, from amino alcohols of the formula IV

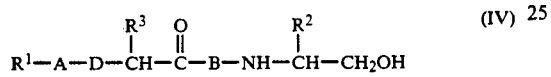

in which $R^1$, $R^2$, $R^3$, A, B and D have the same meaning as in the formula I, by oxidation under conditions as are known from the literature for the conversion of N-protected 2-amino alcohols into N-protected 2-amino aldehydes, or from amino acid derivatives of the formula V

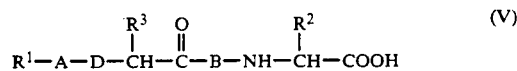

in which $R^1$, $R^2$, $R^3$, A, B and D have the same meaning as in the formula I, by one- or two-stage reduction under conditions as known from the literature for the conversion of N-protected amino acids into N-protected 2-amino aldehydes.

It is particularly advantageous to prepare the aldehydes of the formula II from the carboxylic acids of the formula V by successive reaction with N,O-dimethylhydroxylamine and subsequent reduction of the resulting N,O-dimethylhydroxyamide with lithium aluminum hydride or sodium bis(2-methoxyethoxy)dihydroaluminate by the method of Castro et al., Synthesis 1983, 676.

The carboxylic acids of the general formula V can in turn be advantageously prepared by coupling a fragment with a terminal carboxyl group of the formula VIa or VIb

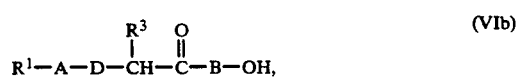

in which $R^1$, $R^3$, A, B and D have the same meaning as in formula I, or a reactive derivative of this fragment, with a corresponding fragment with a free amino group of the formula VIIa or VIIb

in which $R^2$ and B have the same meaning as in formula I, where appropriate a protective group being temporarily introduced to protect the carboxyl group in VIIa and VIIb and being eliminated again after the coupling has been carried out, in analogy to the fragment couplings explained hereinafter for process variant b).

The fragments which are mentioned under process variant b) of a compound of the formula I with a terminal carboxyl group have the formulae VIa and VIb. Fragments of a compound of the formula I with a terminal amino group have the following formulae VIIIa and VIIIb.

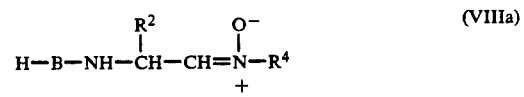

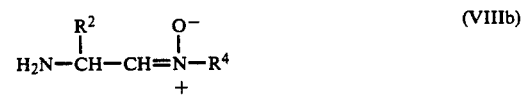

Methods suitable for the preparation of an amide linkage are described, for example, in Houben-Weyl, Methoden der organischen Chemie (Methods of Organic Chemistry), volume 15/2; Bodanszky et al., Peptide Synthesis, 2nd ed. (Wiley & Sons, New York 1976) or Gross, Meienhofer, The Peptides. Analysis, synthesis, biology (Academic Press, New York 1979). The following methods are preferably employed: active ester method with N-hydroxy-succinimide as ester component, coupling with a carbodiimide such as dicyclohexylcarbodiimide or with propanephosphonic anhydride and the mixed anhydride method with pivaloyl chloride.

Fragments of the formula VIIIa and VIIIb can be prepared from protected amino aldehydes by reaction with hydroxylamines of the formula III under conditions analogous to those described under process variant a), followed by an elimination of the protective group.

The hydroxylamine derivatives of the formula III are mostly known from the literature or can be obtained in a way analogous to the known compounds, for example by reduction of the corresponding oxime derivatives with boron hydride/tetrahydrofuran. Hydroxylamine derivatives of the formula III in which $R^4$ carries a carboxy-$(C_1-C_4)$alkoxycarbonyl or $-CONR^5R^6$ substituent in the α-position are N-hydroxyamino acid derivatives whose preparation is likewise known from the literature (for example H. C. J. Ottenheijm et al., Chem. Rev. 86, 697 (1986)) or can be carried out in an analogous manner.

The operations required before and after the preparation of the compounds of the formula I, such as introduction and elimination of protective groups, are known from the literature and are described, for example, in T. W. Greene, "Protective Groups in Organic Synthesis". Salts of compounds of the formula I with salt-forming groups are prepared in a manner known per se, by, for example, reacting a compound of the formula I with a basic group with a stoichiometric amount of a suitable acid. Mixtures of stereoisomers, in particular mixtures of diastereomers, can be separated in a manner known per se by fractional crystallization or by chromatography.

It is possible in an obtainable compound of the formula I to oxidize a thio group to a sulfinyl or sulfonyl group, or a sulfinyl group to a sulfonyl group.

The oxidation to the sulfonyl group can be carried out with most of the customary oxidizing agents. The oxidizing agents preferably used are those which oxidize the thio group or sulfinyl group selectively in the presence of other functional groups of the compound of the formula I, for example of the amide functionality and the hydroxyl group, for example aromatic or aliphatic peroxycarboxylic acids, for example, perbenzoic acid, monoperphthalic acid, m-chloroperbenzoic acid, peracetic acid, performic acid or trifluoroperacetic acid.

The compounds of the formula I according to the invention show enzyme-inhibiting properties; in particular they inhibit the action of the natural enzyme renin and retroviral proteases such as, for example, HIV protease. Renin is a proteolytic enzyme from the class of aspartyl proteases which is secreted as a consequence of various stimuli (volume depletion, sodium deficiency, $\beta$-receptor stimulation) from the juxtaglomerular cells of the kidney into the blood circulation. There it eliminates the decapeptide angiotensin I from the angiotensinogen which is secreted by the liver. This decapeptide is converted by "angiotensin converting enzyme" (ACE) into angiotensin II. Angiotensin II plays an essential part in the regulation of blood pressure, because it raises the blood pressure directly by vasoconstriction. In addition, it stimulates the secretion of aldosterone from the adrenal and, in this way, via inhibition of sodium excretion, increases the extracellular fluid volume, which in turn contributes to raising the blood pressure. Inhibitors of the enzymatic activity of renin bring about a reduced formation of angiotensin I, the consequence of which is a reduced formation of angiotensin II. The lowering of the concentration of this active peptide hormone is the direct cause of the action of renin inhibitors to lower blood pressure.

The activity of renin inhibitors can be examined by in vitro tests. These entail measurement of the reduction in the formation of angiotensin I in various systems (human plasma, purified human renin).

1. Principle of the Test

For example human plasma which contains both renin and angiotensinogen is incubated at 37° C. with the compound to be tested. During this, angiotensin I is liberated from angiotensinogen under the action of renin and can subsequently be measured with a commercially available radioimmunoassay. This angiotensin liberation is inhibited by renin inhibitors.

2. Obtaining the Plasma

The blood is obtained from volunteer subjects (about 0.5 l per person; bluco sampler supplied by ASID Bonz und Sohn, Unterschleissheim) and collected in partially evacuated bottles while cooling in ice. Coagulation is prevented by addition of EDTA (final concentration 10 mM). After centrifugation (HS 4 (Sorvall) rotor, 3500 rpm, 0°–4° C., 15 min; repeat if necessary) the plasma is cautiously removed by a pipette and frozen in suitable portions at −30° C. Only plasmas with sufficiently high renin activity are used for the test. Plasmas with a low renin activity are activated by a cold treatment (−4° C., 3 days) (prorenin→renin).

3. Test Procedure

Angiotensin I is determined using the renin-Maia ® kit (Serono Diagnostics S.A., Coinsins, Switzerland). The plasma is incubated in accordance with the instructions given therein:

Incubation mixture

1000 μl of plasma (thawed at 0°–4° C.)
100 μl of phosphate buffer (pH 7.4)
(Addition of $10^{-4}$M ramiprilate)
10 μl of PMSF solution
10 μl of 0.1% genapol PFIC
12 μl of DMSO or test product The test products are generally made into a $10^{-2}$M solution in 100% dimethyl sulfoxide (DMSO) and diluted appropriately with DMSO; the incubation mixture contains a maximum of 1% DMSO.

The mixtures are mixed in ice and, for the incubation, placed in a water bath (37° C.) for 1 hour. A total of 6 samples (100 μl each) are taken from an additional mixture without inhibitor and without further incubation for determination of the initial angiotensin I content of the plasma used.

The concentrations of the test products are chosen such that the range of 10–90% enzyme inhibition is approximately covered (at least five concentrations). At the end of the incubation time, three 100 μl samples from each mixture are frozen in precooled Eppendorf tubes on dry ice and stored at about −25° C. for the antiogensin I determination (mean from three separate samples).

Angiotensin I Radioimmunoassay (RIA)

The instructions for use of the RIA kit (renin-Maia ® kit, Serono Diagnostics S.A., Coinsins, Switzerland) are followed exactly.

The calibration plot covers the range from 0.2 to 25.0 ng of angiotensin I per ml. The baseline angiotensin I content of the plasma is subtracted from all the measurements. The plasma renin activity (PRA) is reported as ng of Ang I/ml × hour. PRA values in the presence of the test substances are related to a mixture without inhibitor (=100%) and reported as % activity remaining. The $IC_{50}$ value is read off from the plot of % activity remaining against the concentration (M) of the test product (logarithmic scale).

The compounds of the general formula I described in the present invention show inhibitory actions at concentrations of about $10^{-5}$ to $10^{-10}$ mol/l in the in vitro test.

Renin inhibitors bring about a lowering of blood pressure in salt-depleted animals. Because human renin differs from the renin of other species, primates (marmosets, Rhesus monkeys) are employed in the in vivo test of renin inhibitors. Primate renin and human renin have substantially homologous sequences. Endogenous renin release is stimulated by i.v. injection of furosemide. The test compounds are subsequently administered by continuous infusion, and their action on the blood pressure and heart rate is measured. The compounds of the present invention are active in this test in a dose range of about 0.1–5 mg/kg i.v. and on intraduodenal administration by gastroscope in the dose range of about 1-50 mg/kg. The compounds of the general formula I described in the present invention can be used as antihypertensives and for the treatment of cardiac insufficiency.

Besides the renin-inhibitory action, the compounds of the formula I also exhibit an inhibitory action on other aspartyl proteases such as, for example, retroviral proteases, specifically on HIV protease.

HIV protease is cut autocatalytically out of the GAG-POL polypeptide and subsequently cleaves the precursor peptide p55 into the core antigens p17, p24 and p14. It is thus an essential enzyme, inhibition of which interrupts the life cycle of the virus and suppresses its multiplication.

The action of inhibiting HIV protease has particular importance and qualifies the compounds according to the invention in particular for the therapy and prophylaxis of diseases caused by infection with HIV. The compounds of the general formula I according to the invention show inhibitory actions at concentrations of about $10^{-4}$ to $10^{-8}$ mol/l in the in vitro test used.

The invention furthermore relates to the use of compounds of the formula I for the preparation of pharmaceuticals for the therapy of high blood pressure and the treatment of cardiac insufficiency as well as for the therapy and prophylaxis of viral diseases, in particular of diseases caused by HIV, as well as the said pharmaceuticals.

Pharmaceutical products contain an effective amount of the active substance of the formula I together with an inorganic or organic excipient which can be used in pharmacy. Intranasal, intravenous, subcutaneous or oral use is possible. The dosage of the active substance depends on the warm-blooded species, the body weight, age and the mode of administration.

The pharmaceutical products of the present invention are prepared in dissolving, mixing, granulating or coating processes known per se.

For a form for oral use, the active compounds are mixed with the additives customary for this purpose, such as excipients, stabilizers or inert diluents, and converted by customary methods into suitable dosage forms such as tablets, coated tablets, hard gelatin capsules, aqueous, alcoholic or oily suspensions or aqueous, alcoholic or oily solutions. Examples of inert vehicles which can be used are gum arabic, magnesia, magnesium carbonate, potassium phosphate, lactose, glucose, magnesium stearyl fumarate or starch, especially corn starch. This preparation can be carried out both as dry and wet granules. Examples of suitable oily excipients or solvents are vegetable or animal oils, such as sunflower oil and fish liver oil.

For subcutaneous or intravenous administration, the active compounds, or the physiologically tolerated salts thereof, are converted into solutions, suspensions or emulsions, if desired with the substances customary for this purpose, such as solubilizers, emulsifiers or other auxiliaries. Examples of suitable solvents are: water, physiological sodium chloride solutions or alcohols, for example ethanol, propanediol or glycerol, as well as sugar solutions such as glucose or mannitol solutions, or else a mixture of the various solvents mentioned.

List of abbreviations used

Boc: tert.-Butoxycarbonyl
Cha: L-Cyclohexylalanine
TLC: Thin-layer chromatography
DCC: Dicyclohexylcarbodiimide
DCI: Desorption Chemical Ionization
DME: 1,2-Dimethoxyethane
DMF: Dimethylformamide
DNP: 2,4-Dinitrophenyl
EA: Ethyl acetate
EI: Electron Impact
EtOH: Ethanol
FAB: Fast atom bombardment
HOBt: 1-Hydroxybenzotriazole
Iva: Isovaleroyl
LAH: Lithium aluminum hydride
M: Molecular peak
MCPBA: 3-Chloroperbenzoic acid
MeOH: Methanol
MS: Mass spectrum
NEM: N-ethylmorpholine
R.T.: Room temperature
CC: Column chromatography
m.p.: Melting point
Thi: β-2-Thienylalanine
THF: Tetrahydrofuran The other abbreviations used for amino acids correspond to the three-letter code customary in peptide chemistry, as is described, for example, in Eur. J. Biochem. 138, 9-37 (1984). Unless expressly indicated otherwise, the amino acids are always in the L configuration.

The examples which follow serve to illustrate the present invention without restricting it thereto.

EXAMPLE 1

N-[3-Cyclohexyl-2S-[N-(isovaleroyl-L-phenylalanyl-L-norvalyl)amino]propylidene]-N-(1S-ethoxycarbonyl-2-ethyl-1-propyl)amine N-oxide 1a) Boc-Cha N,O-dimethylhydroxylamide 100 g (0.37 mol) of Boc-Cha-OH and 38 g (0.39 mol) of N,O-dimethylhydroxylamine are dissolved in 500 ml of absolute methylene chloride and, while cooling slightly, 232 ml (1.68 mol) of triethylamine are added dropwise. Subsequently, at 0° C., 240 ml of a solution of propane phosphonic anhydride in methylene chloride (50%) are added dropwise within 90 minutes, and the mixture is stirred at R.T. for 4 hours. Then 500 ml of water are added, and the organic phase is separated off, washed three times each with saturated sodium carbonate solution, saturated sodium bicarbonate solution and saturated sodium chloride solution, dried and concentrated. 95.9 g of the title compound are obtained as a yellow oil.

$[\alpha]_D^{25} = -11.8°$ (c=1, methanol)

1b) H-Cha N,O-dimethylhydroxylamide)

50 ml of HCl-saturated DME are added to a solution of 5.5 g (17.5 mmol) of Boc-Cha N,O-dimethylhydroxylamide in 50 ml of DME, and the mixture is stirred at R.T. for 90 minutes. The solvent is evaporated off, and the residue is evaporated to dryness with toluene three times. 4.35 g of the title compound are obtained as the hydrochloride.

m.p. 145°-152° C.

1c) Iva-Phe-Nva-Cha N,O-dimethylhydroxylamide 6.48 ml (51 mmol) of NEM are added to a solution of 5.9 g (17 mmol) of Iva-Phe-Nva-OH, 4.25 g (17 mmol) of H-Cha N,O-dimethylhydroxylamide hydrochloride, 2.75 g (20.4 mmol) of HOBt and 4.2 g (20.4 mmol) of DCC in 40 ml of absolute DMF, and the mixture is stirred at R.T. for two days. The precipitate is filtered off, the filtrate is evaporated, the residue is taken up in EA, the solution is washed with 10% strength citric acid solution, saturated sodium bicarbonate solution and saturated sodium chloride solution, dried and concentrated, and the remaining crude product (10.9 g) is purified by CC on silica gel (methylene chloride/EA 1:1). 7.0 g of the title compound are obtained.

MS (FAB)=545 (M+1)

1d) Iva-Phe-Nva-Cha-H

A solution of 640 mg (1.18 mmol) of Iva-Phe-Nva-Cha-N,O-dimethylhydroxylamide in 3.2 ml of absolute THF is added dropwise to a suspension of 60.8 mg (1.59 mmol) of LAH in 1.6 ml of absolute THF at −5° C.; after 2.5 hours at 0° C., a further 30.5 mg (0.8 mmol) of LAH are added, and the mixture is stirred at 0° C. for a further 30 minutes, cooled to −10° C. and 1.08 ml of saturated Seignette salt solution is slowly added dropwise, and the mixture is stirred for 30 minutes and then 2.46 ml of 2N sulfuric acid are added dropwise. EA is poured onto the reaction mixture, which is stirred for 30 minutes, the solution is decanted off from the precipitate, and the residue is extracted twice with EA. The combined organic phases are washed with water, saturated sodium bicarbonate solution and saturated sodium chloride solution, dried and concentrated at R.T. 470 mg of the title compound are obtained and rapidly reacted further.

MS (FAB)=486 (M+1)

1e) N-(4-Methoxybenzylidene)Val-OEt 4.2 ml (30 mmol) of triethylamine are added to a solution of 6.51 g (30 mmol) of H-Val-OEt hydrochloride and 4.08 g (30 mmol) of 4-methoxybenzaldehyde in 30 ml of absolute methylene chloride, and the mixture is stirred at R.T. overnight. The reaction solution is extracted by shaking twice with water, dried and concentrated. 7.0 g of the title compound, which is still contaminated with about 15% aldehyde, are obtained.

MS (EI)=263 (M+)

1f) 2-(1S-Ethoxycarbonyl-2-methylpropyl)-3-(4-methoxybenzyl)-oxaziridine 8.9 g (33.8 mmol) of N-(4-methoxybenzylidene)-Val-OEt are added slowly at 0° C. to a solution of 6.9 g (33.8 mmol) of MCPBA (85%) in 40 ml of absolute methylene chloride, and the mixture is stirred at 0° C. for 2 hours. The precipitate is filtered off with suction, and the filtrate is washed twice with saturated sodium bicarbonate solution and once with water, dried and concentrated. 8.9 g of the title compound are obtained.

MS (EI)=279 (M+)

1g) HO-Val-OEt 2.93 g (43 mmol) of hydroxylamine hydrochloride are added, while cooling in ice, to a solution of 8.9 g (32 mmol) of 2-(1S-ethoxycarbonyl-2-methylpropyl)-3-(4-methoxybenzyl)-oxaziridine in 32 ml of ethanol, and the mixture is stirred at R.T. overnight. The solvent is evaporated off, the residue is dissolved in 40 ml of methylene chloride, and the remaining precipitate is filtered off with suction. The filtrate is concentrated, the residue is taken up in ether, and the precipitate which separates out after some time is filtered off with suction and dried. To remove 4-methoxybenzaldoxime, it is once more stirred in 15 ml of EA at R.T. for 2 hours and filtered off with suction. 2.45 g of the title compound are obtained as the hydrochloride of sufficient purity for the subsequent reactions.

m.p. 127°–129° C.

1h) N-[3-Cyclohexyl-2S(Iva-Phe-Nva-amino)propylidene]-N-(1S-ethoxycarbonyl-2-methyl-1-propyl)amine N-oxide 500 mg (1.03 mmol) of Iva-Phe-Nva-Cha-H are dissolved in 5 ml of absolute DMF, 222 mg (1.11 mmol) of HO-Val-OEt-hydrochloride are added, and the mixture is stirred at R.T. for 20 hours. The solvent is evaporated off, the residue is taken up in EA, the solution is washed with saturated sodium bicarbonate solution, water and saturated sodium chloride solution, dried and concentrated, and the crude product (402 mg) is purified by CC on silica gel (methylene chloride/MeOH 98/2). 39 mg of the title compound are obtained.

MS (FAB)=629 (M+1)

EXAMPLE 2

N-[3-Cyclohexyl-2S-[N-(isovaleroyl-L-phenylalanyl-L-norvalyl)amino]propylidene]-cyclohexylmethylamine N-oxide

2a) Cyclohexanecarbaldoxime 11.2 g (0.1 mol) of freshly distilled cyclohexanecarbaldehyde are dissolved in 25 ml of MeOH and, at R.T., 13.8 g (0.2 mol) of hydroxylamine hydrochloride and 14.35 g (0.0175 mol) of sodium acetate, dissolved together in 40 ml of water, are added. After four and a half hours at R.T., the oil which has separated out is removed, the aqueous phase is extracted twice with ether, and the combined organic phases are washed with water and saturated sodium chloride solution, dried and concentrated. 12.3 g of the title compound are obtained.

MS (DCI)=128 (M+1).

2b) N-(Cyclohexylmethyl)hydroxylamine 96 ml (96 mmol) of borane solution (1M in THF) are added dropwise at 0° C. within 30 minutes to 7.15 g (56.5 mmol) of cyclohexanecarbaldoxime, and the mixture is then stirred at R.T. for 4 hours. The THF is removed in a rotary evaporator, the residue is cooled to 0° C., and 40 ml of 2N sodium hydroxide solution are slowly added dropwise. The mixture is then heated to reflux for 1 hour, the aqueous phase is extracted continuously with n-pentane for three days, the extract is evaporated, and the crude product (6.1 g) is purified by CC on silica gel (toluene/EtOH 95:5). 3.1 g of the title compound are obtained.

m.p. 61°–63° C.

2c) N-[3-Cyclohexyl-2S-Iva-Phe-Nva)amino-propylidene]-cyclohexylmethylamine N-oxide 200 mg of molecular sieves and 122 mg (0.95 mmol) of n-(cyclohexylmethyl)hydroxylamine are added to a solution of 460 mg (0.95 mmol) of Iva-Phe-Nva-Cha-H in 5 ml of absolute DMF, and the mixture is stirred at R.T. for 20 hours. The reaction solution is filtered, the solvent is evaporated off, and the residue is taken up in EA, when a precipitate separates out. The latter is filtered off with suction (103 mg) and purified by CC on silica gel (methylene chloride/MeOH 9:1). 94 mg of the title compound are obtained.

MS (FAB)=597 (M+1)

EXAMPLE 3

N-[3-Cyclohexyl-2S-[N-(isovaleroyl-L-phenylalanyl-L-norvalyl)amino]propylidene]-methylamine N-oxide 89 mg (1.9 mmol) of N-methylhydroxylamine and 300 mg of anhydrous calcium chloride are added to a solution of 460 mg (0.95 mmol) of Iva-Phe-Nva-Cha-H in 10 ml of ether and 1 ml of absolute DMF, and the mixture is stirred at R.T. for 20 hours. It is filtered, concentrated, and the crude product (265 mg) is purified by CC on silica gel (toluene/EtOH 95:5). 113 mg of the title compound are obtained.

MS (FAB)=515 (M+1)

EXAMPLE 4

N-[3-Cyclohexyl-2S-[N-(isovaleroyl-L-phenylalanyl-L-norvalyl)-amino]propylidene]-isopropylamine N-oxide 200 mg (1.8 mmol) of N-isopropylhydroxylamine hydrochloride are added to a solution of 438 mg (0.9 mmol) of Iva-Phe-Nva-Cha-H in 20 ml of absolute EtOH, and the mixture is stirred at R.T. for 18 hours. The solvent is evaporated off, the residue is partitioned between saturated sodium bicarbonate solution and EA, the aqueous phase is extracted once more with EA, the combined organic phases are washed once with water, dried and concentrated, and the crude product (420 mg) is purified on silica gel (methylene chloride/EA 7:3, then toluene/EtOH 9:1). 223 mg of the title compound are obtained.

MS (FAB)=543 (M+1)

EXAMPLE 5

N-[3-Cyclohexyl-2S-[N-isovaleroyl-L-phenylalanyl-L-norvalyl)amino]propylidene]-N-(1S-ethoxycarbonyl-2-methyl-1-propyl)amine N-oxide

5a) Boc-Cha-H

A solution of 21.0 g (0.067 mol) of Boc-Cha N,O-dimethylhydroxylamide (Example 1a) in 42 ml of absolute THF is added dropwise to a suspension of 3.42 g (0.09 mol) of LAH in 60 ml of absolute THF at −5° C., and the mixture is stirred at 0° C. for 90 minutes. At this temperature, 270 ml of 50% concentrated sodium bisulfate solution are slowly added dropwise, and the mixture is extracted three times with methylene chloride. The combined organic phases are washed with water, dried and concentrated at R.T. 16.9 g of the title compound are obtained and rapidly reacted further.

MS (DCI)=254 (M+1)

5b) N-(2S-Boc-amino-3-cyclohexyl-propylidene)-N-(1S-ethoxycarbonyl-2-methyl-1-propyl)amine N-oxide 1.6 g of HO-Val-OEt are obtained from 2.0 g of HO-Val-OEt hydrochloride (Example 1g) by dissolution in 10 ml of water, saturation with solid sodium bicarbonate, extraction three times with ether, drying and concentration of the combined ethereal phases.

1.5 g of powdered anhydrous calcium chloride and a solution of 1.6 g (10 mmol) of HO-Val-OEt in 50 ml of absolute ether are successively added to a solution of 2.52 g (10 mmol) of Boc-Cha-H in 50 ml of absolute ether at 0° C., and the mixture is stirred at R.T. for 35 hours. The solid is filtered off with suction, the filtrate is concentrated, and the residue is triturated with 50 ml of petroleum ether. The crude product is filtered off with suction and stirred in 20 ml of ether for 1 hour, 20 ml of petroleum ether are added, the solid is again filtered off with suction and washed with a little cold ether. 2.55 g of the title compound are obtained.

MS (DCI)=399 (M+1).

5c) N-(2S-Amino-3-cyclohexyl-propylidene)-N-(1S-ethoxycarbonyl-2-methyl-1-propyl)amine N-oxide 100 mg (0.25 mmol) of N-(2S-Boc-amino-3-cyclohexylpropylidene)-N-(1S-ethoxycarbonyl-2-methyl-1-propyl)-amine N-oxide and 58.2 µl (0.5 mmol) of 2,6-lutidine are dissolved in 1 ml of absolute methylene chloride, and 68 µl (0.375 mmol) of trimethylsilyl triflate are injected. After stirring at R.T. for 100 minutes, a further 68 µl of trimethylsilyl triflate are added, and the mixture is stirred for 10 minutes, after which, according to TLC (toluene/EtOH 8:2), all the starting material has been consumed. 140 µl of MeOH are now injected, and the reaction solution is stirred for 10 minutes, diluted with methylene chloride, washed once with ice-water, dried, concentrated to a volume of about 3 µl and immediately reacted further.

5d) N-[3-cyclohexyl-2S-(Iva-Phe-Nva-amino)propylidene]-N-(1S-ethoxycarbonyl-2-methyl-1-propyl)amine N-oxide 174 mg (0.5 mmol) of Iva-Phe-Nva-OH, 40.3 µl (0.5 mmol) of pyridine and 69.4 µl (0.5 mmol) of N-ethylpiperidine are dissolved in 14 ml of absolute methylene chloride and, at −15° C., 63.4 µl (0.5 mmol) of pivaloyl chloride are added within 5 minutes. The mixture is then stirred at R.T. for 10 minutes and, at 0° C., a freshly prepared solution of about 150 mg (0.5 mmol) of N-(2S-amino-3-cyclohexyl-propylidene)-N-(1S-ethoxycarbonyl-2-methyl-1-propyl)-amine N-oxide in 10 ml of methylene chloride is added. After stirring at R.T. overnight, the solvent is evaporated off, the residue is taken up in ethyl acetate, the solution is washed twice each with 5% strength sodium bisulfate solution, saturated sodium bicarbonate solution and saturated sodium chloride solution, dried and concentrated, and the crude product (167 mg) is purified on silica gel (methylene chloride/EA 9:1). 14 mg of the title compound, which is identical to the product obtained under 1h), are obtained.

EXAMPLE 6

N-[3-Cyclohexyl-2S-N-(tert.[butyloxycarbonyl-L-phenylalanyl-L-histidyl)amino]propylidene]-N-(1S-ethoxycarbonyl-2-methyl-1-propyl)amine N-oxide

6a) H-His(DNP)-OH 4 ml of HCl-saturated dimethoxyethane are added dropwise at 0°–5° C. to a solution of 0.42 g (1 mmol) of Boc-His(DNP)-OH in 5 ml of dimethoxyethane, and the mixture is stirred at 0° 5° C. for 1 hour and at room temperature for 3 hours. The reaction solution is concentrated in vacuo and evaporated to dryness twice more with toluene.

Yield: 0.5 g of the title compound as the hydrochloride.

Rf (methylene chloride/MeOH/AcOH/water 70:30:1)=0.16.

6b) Boc-Phe-His(DNP)-OH 0.362 g (1 mmol) of Boc-Phe hydroxysuccinimide ester, dissolved in 5 ml of ethanol and 5 ml of THF, is added to 0.5 g (1 mmol) of H-His(DNP)-OH hydrochloride in 12.5 ml of a 0.25N sodium bicarbonate solution at room temperature. The reaction mixture is stirred at room temperature for three days. Then 0.83 g of citric acid is added, when the title compound separates out as an oil. The product is extracted with methylene chloride, the organic phase is dried over sodium sulfate and concentrated, a little ethyl acetate is added to the residue, and the title compound is precipitated by addition of diisopropyl ether and is filtered off with suction.

Yield: 0.47 g (83%).

Rf (methylene chloride/MeOH 7:3) 0.43; MS (FAB)=569 (M+1).

6c) N-[3-Cyclohexyl-2S-(Boc-Phe-His(DNP)-amino)-propylidene]-N-(1S-ethoxycarbonyl-2-methyl-1-propyl)-amine N-oxide The title compound is obtained in analogy to the process described in Example 5d) starting from Boc-Phe-His(DNP)-OH and N-(2S-amino-3-cyclohexyl-propylidene)-N-(1S-ethoxycarbonyl-2-methyl-1-propyl)amine N-oxide.

MS (FAB)=849 (M+1).

6d) N-[3-Cyclohexyl-2S-(Boc-Phe-His-amino)-propylidene]-N-(1S-ethoxycarbonyl-2-methyl-2-propyl)amine N-oxide 0.1 ml (1 mmol) of thiophenol is added to 53 mg (0.062 mmol) of DNP-protected product from Example 6c) in 5 ml of acetonitrile, and the mixture is stirred at R.T. for 5 hours. The reaction solution is concentrated in vacuo, and the crude product is purified by CC on silica gel (methylene chloride/MeOH 98:2, 95:5, 9:1). 12 mg of the title compound are obtained.

MS (FAB)=683 (M+1).

EXAMPLE 7

N-[3-Cyclohexyl-2S-[N-(ethylaminocarbonyl-L-phenylalanyl-L-norvalylamino]propylidene]-cyclohexylmethylamine N-oxide

7a) N-(Ethylaminocarbonyl)-Phe-OH 3.37 g (10 mmol) of Phe p-toluenesulfonate are dissolved in 10 ml of absolute tetrahydrofuran and, at room temperature, 2.4 ml (12 mmol) of freshly distilled hexamethyldisilazane are added, and the mixture is stirred for two hours. 0.97 ml (12 mmol) of ethyl isocyanate is added to the suspension, which is left to stand at room temperature overnight. The precipitate is filtered off with suction, the filtrate is cooled in an ice bath, filtered again and concentrated, and the residue is stirred with water. The precipitate is filtered off with suction and dried over phosphorus pentoxide.

Yield: 1.7 g (72%).

Rf (methylene chloride/methanol/water/glacial acetic acid 70:30:1:1)=0.68; MS (DCI)=237 (M+1).

7b) N-(Ethylcarbonylamino)-Phe-Nva-OMe 3.51 ml (25.4 mmol) of absolute triethylamine and 3.30 ml of propanephosphonic anhydride (50% in methylene chloride) are successively added with ice cooling to 1.2 g (5.08 mmol) of N-(ethylaminocarbonyl)-Phe-OH and 0.85 g (5.08 mmol) of L-Nva-OMe hydrochloride in 30 ml of absolute methylene chloride, and the mixture is stirred at room temperature for 6 hours and left to stand overnight. The reaction mixture is hydrolyzed by being poured onto ice-water, and the organic phase is separated off and washed three times each with 100 ml each time of 10% strength citric acid solution, saturated sodium bicarbonate solution and water, dried over sodium sulfate and concentrated. The residue is triturated in a little cold diisopropyl ether, filtered off with suction and dried in vacuo.

Yield: 1.5 g (84%)

Rf (methylene chloride/methanol 9:1)=0.49.

7c) N-(Ethylaminocarbonyl)-Phe-Nva-OH 0.2 g of lithium hydroxide is added to 1.5 g (4.29 mmol) of N-(ethylaminocarbonyl)-Phe-Nva-OMe from Example 1b) in 8 ml of water and 8 ml of dioxane at room temperature, and the mixture is stirred for two hours. The reaction solution is acidified with 10% strength sodium bisulfate solution, and the precipitate is filtered off with suction, triturated with diisopropyl ether and dried.

Yield: 1.3 g.

Rf (toluene/ethanol 8:2)=0.02; MS(DCI) 336 (M+1).

7d) N-(Ethylaminocarbonyl)-Phe-Nva-Cha N,O-dimethylhydroxylamide

The title compound is obtained in analogy to the process described in Example 1c) starting from N-ethylaminocarbonyl-Phe-Nva-OH and H-Cha N,O-dimethylhydroxylamide.

MS (FAB)=566 (M+1).

7e) N-Ethylaminocarbonyl-Phe-Nva-Cha-H

The title compound is obtained in analogy to the process described in Example 1d) by reduction of N-ethylaminocarbonyl-Phe-Nva-Cha N,O-dimethylhydroxylamide.

MS (FAB)=507 (M+1).

7f) N-[3-Cyclohexyl-2S-[N-(ethylaminocarbonyl-Phe-Nva)amino]propylidene]-cyclohexylmethylamine N-oxide The title compound is obtained in analogy to the process described in Example 2c) starting from N-ethylaminocarbonyl-Phe-Nva-Cha-H and N-cyclohexylmethylhydroxylamine.

MS (FAB)=618 (M+1).

The following compounds according to the invention were additionally prepared starting from the appropriate starting materials and using the processes described in the preceding examples.

EXAMPLE 8

N-[3-Cyclohexyl-2S-[N-[N-(2S-benzyl-3-tert.butylsulfonylpropionyl)-L-histidyl]amino]-propylidene]cyclohexylmethyl-amine N-oxide

MS (FAB)=670 (M+1).

EXAMPLE 9

N-[3-Cyclohexyl-2S-[N-(morpholinocarbonyl-L-phenylalanyl-L-histidyl)amino]propylidene]cyclohexylmethyl-amine N-oxide

MS (FAB)=664 (M+1).

EXAMPLE 10

N-[3-Cyclohexyl-2S-[N-(tert.butylaminothiocarbonyl-L-phenylalanyl-L-norvalyl)amino]propylidene]-cyclohexylmethylamine N-oxide

MS (FAB)=628 (M+1).

EXAMPLE 11

N-[2S-[N-(Isovaleroyl-L-phenylalanyl-L-norvalyl)-amino]-4-methylpentylidene]-cyclohexylmethylamine N-oxide

MS (FAB)=557 (M+1).

EXAMPLE 12

N-[2S-[N-(Isovaleroyl-L-phenylalanyl-L-norvalyl)-amino]-3-phenylpropylidene]-cyclohexylmethylamine N-oxide

MS (FAB)=591 (M+1).

EXAMPLE 13

N-[3-Cyclohexyl-2S[N-(isovaleroyl-L-phenylalanyl-L-norvalyl)-amino]-propylidene]-isobutylamine N-oxide

MS (FAB)=557 (M+1).

EXAMPLE 14

N-[3-Cyclohexyl-2S-[N-[N-[2S-(2-thienylmethyl)-3-tert.butylsulfonyl-propionyl]-L-norvalyl]amino]-propylidene]cyclohexylmethylamine N-oxide

MS (FAB)=638 (M+1).

EXAMPLE 15

N-[3-Cyclohexyl-2RS-[N-(isovaleroyl-L-phenylalanyl-L-norvalyl)amino]propylidene]-N-(1S-ethoxycarbonyl-2-methyl-1-propyl)amine-N-oxide

EXAMPLE 16

N-[3-Cyclohexyl-2RS-[N-(isovaleroyl-L-phenylalanyl-L-norvalyl)amino]propylidene]-N-cyclohexylmethylamine N-oxide

MS (FAB)=597 (M+1).

EXAMPLE 17

N-[3-Cyclohexyl-2RS-[isovaleroyl-L-phenylalanyl-L-norvalyl)amino]propylidene]-methylamine N-oxide

MS (FAB)=515 (M+1).

EXAMPLE 18

N-[3-Cyclohexyl-2RS-[N-(isovaleroyl-L-phenylalanyl-L-norvalyl)amino]propylidene]-isopropylamine N-oxide

MS (FAB)=543 (M+1).

EXAMPLE 19

N-[3-Cyclohexyl-2S-[N-(isovaleroyl-L-phenylalanyl-L-histidyl)amino]propyliden]-isobutylamin-N-oxide

MS (FAB)=595 (M+1).

EXAMPLE 20

N-[3-Cyclohexyl-2S-[N-[N-(2S-benzyl-3-tert.butylsulfonylpropionyl)-L-histidyl]amino]propyliden]isobutylamin-N-oxide

MS (FAB)=630 (M+1).

EXAMPLE 21

N-[3-Cyclohexyl-2S-[N-(isovaleroyl-L-phenylalanyl-L-histidyl)amino]propyliden]-N-[2-(2-pyridyl)ethyl]-amin-N-oxide

MS (FAB)=644 (M+1).

We claim:
1. A compound of the formula I

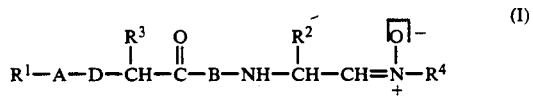

in which
$R^1 = C_1-C_6$-alkyl, $C_1-C_6$-alkoxy, $C_1-C_6$-alkyl-amino,
$R^2 = C_5-C_7$-alkyl-$C_1-C_2$-alkyl,
$R^3$ = phenyl-$C_1-C_2$-alkyl,
$R^4 = C_1-C_6$-alkyl, $C_1-C_4$-alkoxycarbonyl-$C_1-C_6$-alkyl, or $C_5-C_7$-cycloalkyl-$C_1-C_2$-alkyl;
A=CO
V=norvaline or histidine; and
D=NH
or physiologically tolerated salts thereof.

2. A method for the treatment of high blood pressure, which comprises administration of an effective amount of a compound of the formula I as claimed in claim 1, or a physiologically tolerated salt thereof.

3. A pharmaceutical composition for the treatment of high blood pressure comprising an effective amount of a compound of the formula I as claimed in claim 1, or a physiologically tolerated salt thereof, and a pharmaceutically acceptable vehicle.

* * * * *

UNITED STATES PATENT AND TRADEMARK OFFICE
CERTIFICATE OF CORRECTION

PATENT NO.   : 5,185,324
DATED        : February 09, 1993
INVENTOR(S)  : Wolfgang Ruger et al.

It is certified that error appears in the above-identified patent and that said Letters Patent is hereby corrected as shown below:

On the title page, item [75], change "Scholkens" to --Schölkens--.

Claim 1, column 20, line 36, change "$C_5$-$C_7$-alkyl" to --$C_5$-$C_7$-cycloalkyl- --.

Claim 1, column 20, line 41, change "V" to --B--.

Signed and Sealed this

Fourteenth Day of December, 1993

Attest:

BRUCE LEHMAN

*Attesting Officer*     *Commissioner of Patents and Trademarks*